(12) United States Patent
Jackson et al.

(10) Patent No.: US 8,313,911 B2
(45) Date of Patent: Nov. 20, 2012

(54) PRODUCTION OF POLYUNSATURATED FATTY ACIDS IN OLEAGINOUS YEASTS

(75) Inventors: Ethel Noland Jackson, Greenville, DE (US); David Richard Short, Newark, DE (US); Dongming Xie, Newark, DE (US); Zhixiong Xue, Chadds Ford, PA (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 20 days.

(21) Appl. No.: 12/641,929

(22) Filed: Dec. 18, 2009

(65) Prior Publication Data

US 2011/0059204 A1    Mar. 10, 2011
US 2011/0274787 A9    Nov. 10, 2011

Related U.S. Application Data

(60) Continuation-in-part of application No. 12/469,467, filed on May 20, 2009, which is a division of application No. 10/840,579, filed on May 6, 2004, now Pat. No. 7,238,482, and a continuation-in-part of application No. 12/469,494, filed on May 20, 2009.

(60) Provisional application No. 60/468,677, filed on May 7, 2003.

(51) Int. Cl.
     *C12Q 1/68*      (2006.01)
     *C12Q 1/54*      (2006.01)

(52) U.S. Cl. .......................................... 435/6.15; 435/14

(58) Field of Classification Search ........................ None
See application file for complete search history.

(56) References Cited

U.S. PATENT DOCUMENTS

| | | | |
|---|---|---|---|
| 7,364,883 B2 | 4/2008 | Chen | |
| 7,550,286 B2 | 6/2009 | Damude et al. | |
| 7,588,931 B2 | 9/2009 | Damude et al. | |
| 2003/0196217 A1* | 10/2003 | Mukerji et al. | 800/281 |
| 2009/0093543 A1 | 4/2009 | Xue et al. | |
| 2010/0317072 A1* | 12/2010 | Hong et al. | 435/134 |

FOREIGN PATENT DOCUMENTS

| | | |
|---|---|---|
| EP | 0770683 A1 | 5/1997 |
| WO | 2006052870 A2 | 5/2006 |

OTHER PUBLICATIONS

Sharifia et al. Production of ethanol by filamentous and yeast-like forms of Mucor indicus from fructose, glucose, sucrose, and molasses. J Ind Microbiol Biotechnol. Nov. 2008;35(11):1253-9. Epub Aug. 20, 2008.*
Ratledge et al. Industrial Chemicals, Biochemicals and Fuel. Fats and Oils, pp. 983-1003. 1985.*
Forster, A. et al., Citric Acid Production From Sucrose Using A Recombinant Strain of the Yeast Yarrowia Lipolytica, Appl. Microbiol. Biotechnol., vol. 75 (2007), pp. 1409-1417.
Tahoun, M. et al., Influence of Selected Sugars and Temperature on Fatty Acids Composition in Candida Lipolytica, Appl. Microbiol. Biotechnol., vol. 24 (1986), pp. 235-239.
Kautola, H. et al., The Utilization of Beet Molasses in Citric Acid Production With Yeast, Sciences Des Aliments, vol. 12 (1992), pp. 383-392.

* cited by examiner

*Primary Examiner* — Michele K Joike

(57) ABSTRACT

Methods for the production of omega-3 and/or omega-6 fatty acids in oleaginous yeasts grown on a fermentable carbon source selected from the group consisting of invert sucrose, glucose, fructose and combinations of these, provided that glucose is used in combination with invert sucrose and/or fructose. Specifically, methods are provided for production of linoleic acid, eicosadienoic acid, gamma-linolenic acid, dihomo-gamma-linolenic acid, arachidonic acid, n-6 docosapentaenoic acid, α-linolenic acid, stearidonic acid, eicosatrienoic acid, eicosatetraenoic acid, eicosapentaenoic acid, docosapentaenoic acid and docosahexaenoic acid.

7 Claims, 3 Drawing Sheets

PRODUCTION OF POLYUNSATURATED FATTY ACIDS IN OLEAGINOUS YEASTS

CROSS-REFERENCE TO RELATED APPLICATION

This patent application is a continuation-in-part of application Ser. No. 12/469,467 filed May 20, 2009, pending, which was a divisional of application Ser. No. 11/714,377 filed Mar. 5, 2007, granted as U.S. Pat. No. 7,553,628, which was a divisional of application Ser. No. 10/840,579 filed May 6, 2004, granted as U.S. Pat. No. 7,238,482, which claimed the priority benefit of U.S. Provisional Application No. 60/468,677 filed May 7, 2003, now expired.

This patent application is also a continuation-in-part of application Ser. No. 12/469,494 filed May 20, 2009, which was a divisional of application Ser. No. 11/714,377 filed Mar. 5, 2007, granted as U.S. Pat. No. 7,553,628, which was a divisional of application Ser. No. 10/840,579 filed May 6, 2004, granted as U.S. Pat. No. 7,238,482, which claimed the priority benefit of U.S. Provisional Application No. 60/468,677 filed May 7, 2003, now expired.

FIELD OF THE INVENTION

This invention is in the field of biotechnology. More specifically, this invention pertains to the production of long chain polyunsaturated fatty acids (PUFAs) in oleaginous yeasts using carbon sources containing fructose and/or invert sucrose.

BACKGROUND OF THE INVENTION

The health benefits associated with polyunsaturated fatty acids ["PUFAs"], especially ω-3 and ω-6 PUFAs, have been well documented. In order to find ways to produce large-scale quantities of ω-3 and ω-6 PUFAs, researchers have directed their work toward the discovery of genes, the understanding of the encoded biosynthetic pathways that result in lipids and fatty acids, and genetic engineering techniques to introduce these biosynthetic pathways into preferred host organisms.

A variety of different hosts including plants, algae, fungi, stramenopiles and yeast are being investigated as means for commercial PUFA production. Genetic engineering has demonstrated that the natural abilities of some hosts, even those natively limited to linoleic acid ["LA"; 18:2 ω-6] or α-linolenic acid ["ALA"; 18:3 ω-3] fatty acid production, can be substantially altered to result in high-level production of various long-chain ω-3/ω-6 PUFAs.

Although the literature reports a number of recent examples whereby various portions of the ω-3/ω-6 PUFA biosynthetic pathway have been introduced into various hosts, significant efforts by Applicants' Assignee have focused on using the oleaginous yeast, *Yarrowia lipolytica* (formerly classified as *Candida lipolytica*). Oleaginous yeasts are defined as those yeasts that are naturally capable of or engineered to be capable of oil synthesis and accumulation, wherein oil accumulation is at least 25% of the cellular dry weight.

For example, U.S. Pat. No. 7,238,482 demonstrated the feasibility of producing omega-6 and omega-3 fatty acids in *Yarrowia lipolytica*. Intl. App. Pub. No. WO 2006/052870 demonstrated production of 28.1% EPA of total fatty acids in a recombinant *Yarrowia lipolytica* strain; U.S. Pat. No. 7,588,931 demonstrated production of 14% ARA of total fatty acids in a recombinant *Yarrowia lipolytica* strain; U.S. Pat. No. 7,550,286 demonstrated production of 5% DHA of total fatty acids in a recombinant *Yarrowia lipolytica* strain. And, U.S. Pat. Appl. Pub. No. 2009-0093543-A1 describes optimized recombinant *Yarrowia lipolytica* strains for EPA production and demonstrated production of up to 55.6% EPA of total fatty acids. In all of these methods, however, the production of PUFAs was demonstrated using oleaginous yeast grown using glucose as the carbon source.

It would be advantageous to produce PUFAs using carbon sources other than glucose, such as fructose and invert sucrose, because this would enable one to choose the most economical carbon source for a particular geographical region. For example, in regions such as South America, in particular Brazil, sugar cane is plentiful; therefore, invert sucrose would be an economical carbon source for the production of PUFAs.

SUMMARY OF THE INVENTION

The invention provides a method for producing polyunsaturated fatty acids comprising:
  a) providing a transgenic oleaginous yeast which produces at least 25% of its dry cell weight as oil; comprising genes encoding a functional polyunsaturated fatty acid biosynthetic pathway;
  b) growing the yeast of step (a) in the presence of a fermentable carbon source selected from the group consisting of invert sucrose, glucose, fructose and combinations of these whereby polyunsaturated fatty acids are produced provided that glucose is used in combination with invert sucrose and/or fructose; and
  c) optionally, recovering the polyunsaturated fatty acids.

Preferably, the polyunsaturated fatty acids are selected from the group consisting of omega-3 fatty acids, omega-6 fatty acids, and combinations thereof.

The genes encoding a functional omega-3/omega-6 fatty acid biosynthetic pathway can be selected from the group consisting of: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and $C_{20/22}$ elongase.

The preferred oleaginous yeast is selected from the group consisting of *Yarrowia*, *Candida*, *Rhodotorula*, *Rhodosporidium*, *Cryptococcus*, *Trichosporon* and *Lipomyces*. The most preferred oleaginous yeast is *Yarrowia lipolytica*.

In another aspect, the invert sucrose can be a mixture comprising 25 to 50% glucose and 25 to 50% fructose.

Figure 1A:
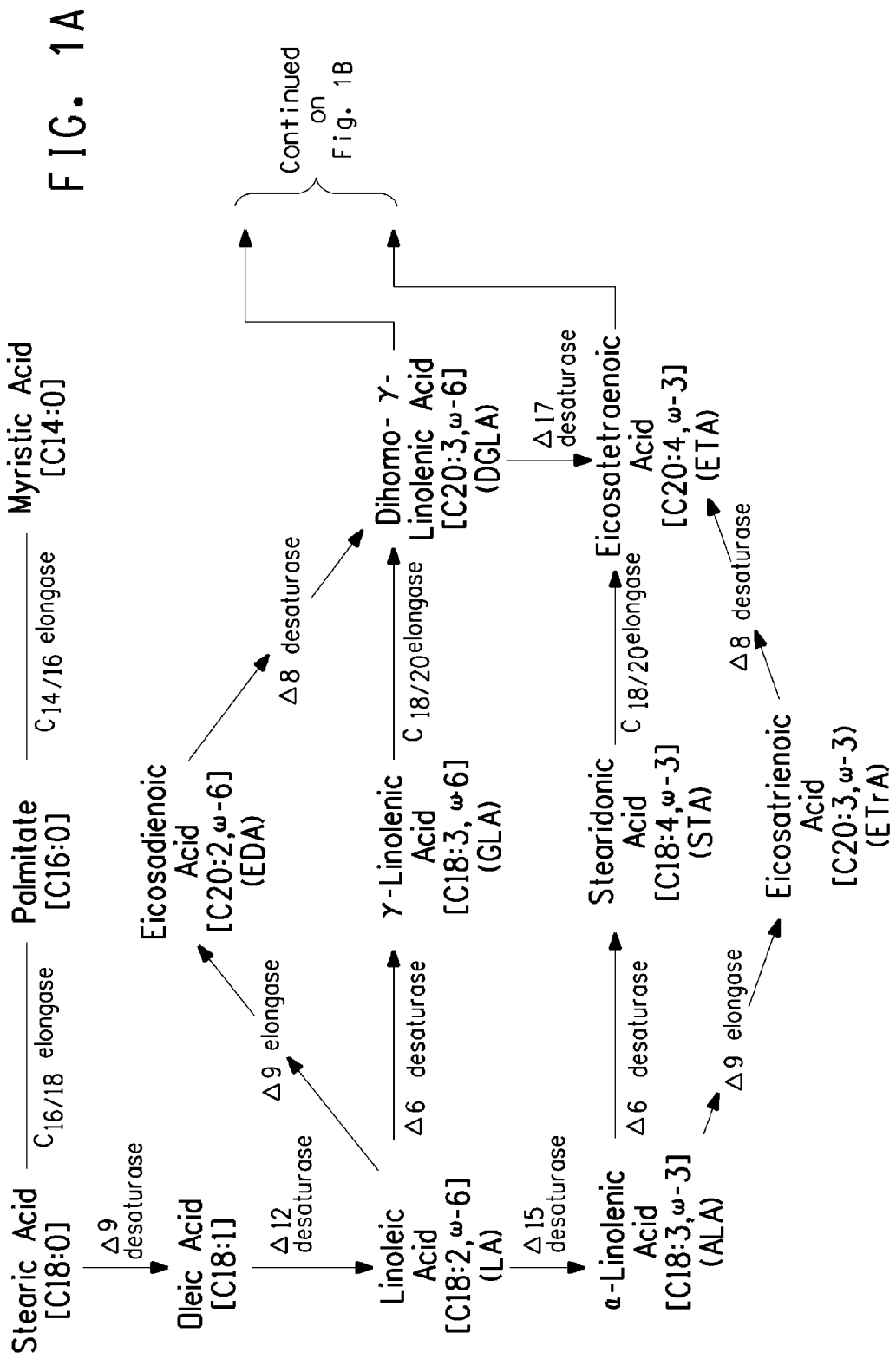
FIG. 1 illustrates the ω-3/ω-6 fatty acid biosynthetic pathway.

The invention can be more fully understood from the following detailed description, which forms a part of this application.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated "ORF".

"Polymerase chain reaction" is abbreviated "PCR".

"Polyunsaturated fatty acid(s)" is abbreviated "PUFA(s)".

"ATCC" refers to The American Type Culture Collection, Manassas, Va.

"Co-enzyme A" is abbreviated as "CoA".

"Total fatty acids" are abbreviated as "TFAs".

"Fatty acid methyl esters" are abbreviated as "FAMEs".

"Dry cell weight" is abbreviated as "DCW".

The terms "ω-3 fatty acids" and "omega-3 fatty acids" are used interchangeably herein.

The terms "ω-6 fatty acids" and "omega-6 fatty acids" are used interchangeably herein.

The terms "Δ" and "delta" are used interchangeably herein when referring to desaturases.

The term "'lipids" refer to any fat-soluble (i.e., lipophilic), naturally-occurring molecule. A general overview of lipids is provided in U.S. Pat. Appl. Pub. No. 2009-0093543-A1 (see Table 2 therein).

The term "oil" refers to a lipid substance that is liquid at 25° C. and usually polyunsaturated. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

The terms "polyunsaturated fatty acid(s)" and "PUFA(s)", as used herein refer to fatty acids having at least 18 carbon atoms and 2 or more double bonds.

Nomenclature used to describe PUFAs herein is given in Table 1. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of the Table summarizes the common names of ω-3 and ω-6 fatty acids and their precursors, the abbreviations that will be used throughout the specification and the chemical name of each compound.

TABLE 1

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-tetraenoic | DTA | cis-7,10,13,16-docosatetraenoic | 22:4 ω-3 |
| Docosa-pentaenoic | DPAn-6 | cis-4,7,10,13,16-docosapentaenoic | 22:5 ω-6 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

The terms "PUFA biosynthetic pathway" and "omega-3/omega-6 fatty acid biosynthetic pathway" are used interchangeably herein and refer to a metabolic process that converts oleic acid to omega-6 fatty acids such as LA, EDA, GLA, DGLA, ARA, DTA and DPAn-6 and omega-3 fatty acids such as ALA, STA, ETrA, ETA, EPA, DPA and DHA. This process is well described in the literature (e.g., see U.S. Pat. Appl. Pub. No. 2006-0115881-A1). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and/or $C_{20/22}$ elongase. The term "functional" as used herein in context with the omega-3/omega-6 fatty acid biosynthetic pathway means that some or all of the genes in the pathway express active enzymes. It should be understood that "omega-3/omega-6 fatty acid biosynthetic pathway" or "functional omega-3/omega-6 fatty acid biosynthetic pathway" does not imply that all the genes listed in this paragraph are required as a number of fatty acid products will only require the expression of a subset of the genes of this pathway.

The term "Δ9 elongase/Δ8 desaturase pathway" refers to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, DTA, DPAn-6, EPA, DPA and DHA may also be synthesized.

The term "delta-6 desaturase/delta-6 elongase pathway" refers to a PUFA biosynthetic pathway that minimally includes at least one delta-6 desaturase and at least one delta-6 elongase, thereby enabling biosynthesis of DGLA and/or ETA from LA and ALA, respectively, with GLA and/or STA as intermediate fatty acids. With expression of other desaturases and elongases, ARA, DTA, DPAn-6, EPA, DPA and DHA may also be synthesized.

The term "desaturase" refers to a polypeptide component of a multi-enzyme complex that can desaturate, i.e., introduce a double bond in one or more fatty acids to produce a mono- or polyunsaturated fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: 1) $\Delta 17$ desaturases that desaturate a fatty acid between the 17th and 18th carbon atom numbered from the carboxyl-terminal end of the molecule and which, for example, catalyze the conversion of ARA to EPA and/or DGLA to ETA; 2) $\Delta 6$ desaturases that catalyze the conversion of LA to GLA and/or ALA to STA; 3) $\Delta 5$ desaturases that catalyze the conversion of DGLA to ARA and/or ETA to EPA; 4) $\Delta 4$ desaturases that catalyze the conversion of DPA to DHA; 5) $\Delta 12$ desaturases that catalyze the conversion of oleic acid to LA; 6) $\Delta 15$ desaturases that catalyze the conversion of LA to ALA; 7) $\Delta 9$ desaturases that catalyze the conversion of palmitate to palmitoleic acid (16:1) and/or stearate to oleic acid (18:1); and 8) delta-8 desaturases that catalyze the conversion of EDA to DGLA and/or ETrA to ETA.

The term "elongase" refers to a polypeptide that can elongate a fatty acid carbon chain to produce an acid 2 carbons longer than the fatty acid substrate that the elongase acts upon. This process of elongation occurs in a multi-step mechanism in association with fatty acid synthase, as described in Intl. App. Pub. No. WO 2005/047480. Examples of reactions catalyzed by elongase systems are the conversion of GLA to DGLA, STA to ETA, ARA to DTA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA, LA, ALA) and a $C_{20/22}$ elongase [also referred to as a $\Delta 5$ elongase] will utilize a $C_{20}$ substrate (e.g., ARA, EPA). For the purposes herein, two distinct types of $C_{18/20}$ elongases can be defined: a $\Delta 6$ elongase will catalyze conversion of GLA and STA to DGLA and ETA, respectively, while a $\Delta 9$ elongase is able to catalyze the conversion of LA and ALA to EDA and ETrA, respectively.

The term "oleaginous" refers to those organisms that tend to store their energy source in the form of oil (Weete, In: *Fungal Lipid Biochemistry*, 2nd Ed., Plenum, 1980). Generally, the cellular oil content of oleaginous microorganisms follows a sigmoidal curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). It is common for oleaginous microorganisms to accumulate in excess of about 25% of their dry cell weight as oil.

The term "oleaginous yeast" refers to those microorganisms classified as yeasts that can make oil or those yeasts that can be engineered to make oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon source" means a carbon source that a microorganism will metabolize to derive energy. For use in the method of the invention, the fermentable carbon source is selected from the group consisting of invert sucrose, glucose, fructose and combinations of these, provided that glucose is used in combination with invert sucrose and/or fructose.

The term "invert sucrose", also referred to herein as "invert sugar", refers to a mixture comprising equal parts of fructose and glucose resulting from the hydrolysis of sucrose. Invert sucrose may be a mixture comprising 25 to 50% glucose and 25 to 50% fructose. Invert sucrose may also comprise sucrose, the amount of which depends on the degree of hydrolysis.

The terms "host cell" and "host organism" are used interchangeably herein and refer to a microorganism capable of receiving foreign or heterologous genes and capable of expressing those genes to produce an active gene product.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine "Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" are used interchangeably herein and refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Disclosed herein are methods for the production of omega-3 and/or omega-6 fatty acids in oleaginous yeasts grown on a fermentable carbon source selected from the group consisting of invert sucrose, glucose, fructose and combinations of these, provided that glucose is used in combination with invert sucrose and/or fructose. Specifically, methods are provided for production of LA, GLA, DGLA, EDA, ARA, DPA n-6, ALA, STA, ETrA, ETA, EPA, DPA n-3 and DHA. This is accomplished by introduction of a PUFA biosynthetic pathway into oleaginous yeast hosts, as described below. Thus, this disclosure demonstrates that oleaginous yeasts can be engineered to enable production of any PUFA composition that is desired from the aforementioned fermentable carbon sources.

In general, lipid accumulation in oleaginous microorganisms is triggered in response to the overall carbon to nitrogen ratio present in the growth medium. When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol and subsequent cleavage of the citrate by ATP-citrate lyase to yield acetyl-CoA and oxaloacetate. Acetyl-CoA is the principle building block for de novo biosynthesis of fatty acids. Any compound that can be effectively metabolized to produce acetyl-CoA, e.g., glucose and fructose, can serve as a precursor of fatty acids. Since acetyl-CoA cannot be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which can be summarized as described below (Smith, S. *FASEB J.*, 8(15):1248-59 (1994)). First, acetyl-CoA and malonyl-CoA are transferred to the acyl carrier peptide (ACP) of FAS. The acetyl group is then transferred to the malonyl group, forming β-ketobutyryl-ACP and releasing $CO_2$. The β-ketobutyryl-ACP undergoes reduction (via β-ketoacyl reductase) and dehydration (via β-hydroxyacyl dehydratase) to form a trans-monounsaturated fatty acyl group. The double bond is reduced by NADPH, yielding a saturated fatty-acyl group two carbons longer than the initial one. The ability of the butyryl-group to condense with a new malonyl group and repeat the elongation process is then regenerated. When the fatty acyl group becomes 16 carbons long, a thioesterase activity hydrolyses it, releasing free palmitate.

Palmitate (16:0) is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate are converted to their unsaturated derivatives, palmitoleic (16:1) and oleic (18:1) acids, respectively, by the action of a Δ9 desaturase.

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid). The phosphate is then removed, by phosphatidic acid phosphatase, to yield 1,2-diacylglycerol. Triacylglycerol is formed upon the addition of a third fatty acid by the action of a diacylglycerol-acyl transferase.

A wide spectrum of fatty acids (including saturated and unsaturated fatty acids and short-chain and long-chain fatty acids) can be incorporated into TAGs, the primary storage unit for fatty acids. In the methods and host cells described herein, incorporation of PUFAs into TAGs is most desirable, although the structural form of the PUFA is not limiting (thus, for example, the EPA may exist in the total lipids as free fatty acids or in esterified forms such as acylglycerols, phospholipids, sulfolipids or glycolipids).

Although most PUFAs are incorporated into TAGs as neutral lipids and are stored in lipid bodies, it is important to note that a measurement of the total PUFAs within an oleaginous organism should minimally include those PUFAs that are located in the phosphatidylcholine, phosphatidylethanolamine, and TAG fractions.

The metabolic process wherein oleic acid is converted to PUFAs involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, multiple alternative pathways exist for PUFA production.

Figure 1B:
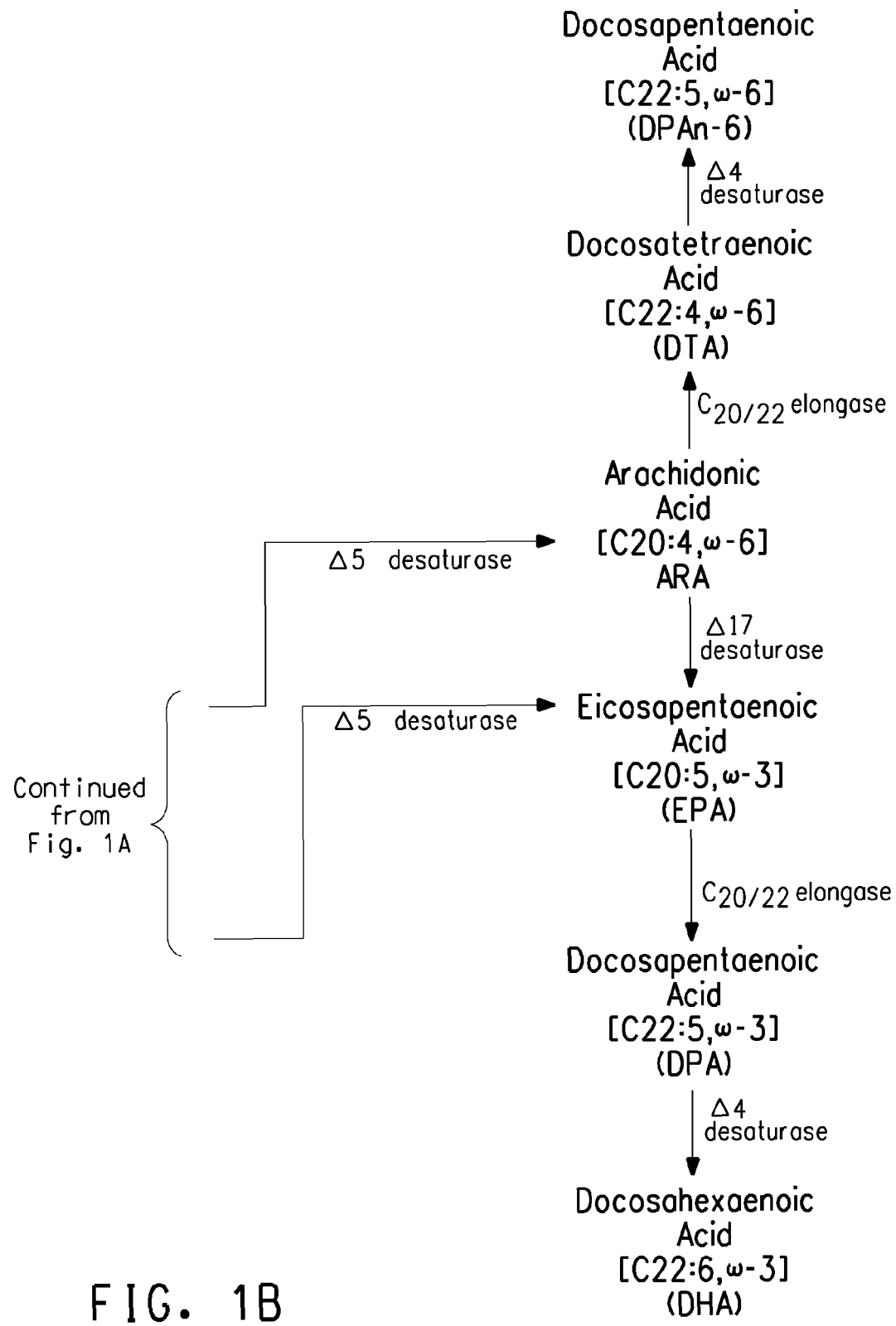

Specifically, FIG. 1 depicts the pathways described below. All pathways require the initial conversion of oleic acid to linoleic acid ["LA"], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"] by a delta-9 elongase; 2) EDA is converted to dihomo-gamma-linolenic acid ["DGLA"] by a delta-8 desaturase; 3) DGLA is converted to arachidonic acid ["ARA"] by a delta-5 desaturase; 4) ARA is converted to docosatetraenoic acid ["DTA"] by a $C_{20/22}$ elongase; and, 5) DTA is converted to docosapentaenoic acid ["DPAn-6"] by a delta-4 desaturase.

The "delta-9 elongase/delta-8 desaturase pathway" can also use alpha-linolenic acid ["ALA"] as substrate to produce long-chain omega-3 fatty acids as follows: 1) LA is converted to ALA, the first of the omega-3 fatty acids, by a delta-15 desaturase; 2) ALA is converted to eicosatrienoic acid ["ETrA"] by a delta-9 elongase; 3) ETrA is converted to eicosatetraenoic acid ["ETA"] by a delta-8 desaturase; 4) ETA is converted to eicosapentaenoic acid ["EPA"] by a delta-5 desaturase; 5) EPA is converted to docosapentaenoic acid ["DPA"] by a $C_{20/22}$ elongase; and, 6) DPA is converted to docosahexaenoic acid ["DHA"] by a delta-4 desaturase. Optionally, omega-6 fatty acids may be converted to omega-3 fatty acids. For example, ETA and EPA are produced from DGLA and ARA, respectively, by delta-17 desaturase activity. Advantageously for the purposes herein, the delta-9 elongase/delta-8 desaturase pathway enables production of a PUFA oil that lacks significant amounts of gamma-linolenic acid ["GLA"].

Alternative pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"], respectively, by a delta-6 desaturase; then, a $C_{18/20}$ elongase converts GLA to DGLA and/or STA to ETA.

In some cases, the oleaginous yeast in which it is desirable to produce PUFAs will possess endogenous genes encoding some PUFA biosynthetic pathway enzymes. For example, oleaginous yeast can typically produce 18:2 fatty acids (and some have the additional capability of synthesizing 18:3 fatty acids); thus, oleaginous yeast typically possess native Δ12 desaturase activity and may also have Δ15 desaturases. In some embodiments, therefore, expression of the native desaturase enzyme is preferred over a heterologous (or "foreign") enzyme since: 1) the native enzyme is optimized for interaction with other enzymes and proteins within the cell; and 2) heterologous genes are unlikely to share the same codon preference in the host organism. Additionally, advantages are incurred when the sequence of the native gene is known, as it permits down-regulation of the endogenous gene.

In many instances, the appropriate desaturases and elongases are not present in the host organism of choice to enable production of the desired PUFA products. Oleaginous yeast can be engineered to produce ω-3/ω-6 PUFAs by integration of appropriate heterologous genes encoding desaturases and elongases of the Δ6 desaturase/Δ6 elongase pathway or the Δ9 elongase/Δ8 desaturase pathway into the host organism for production of any particular PUFA of interest. Preferred genes, considerations for choosing a specific polypeptide having desaturase or elongase activity, and means to engineer a PUFA biosynthetic pathway into an oleaginous yeast are detailed in U.S. Pat. Nos. 7,238,482, 7,465,564, 7,588,931 and 7,550,286, and U.S. Pat. Appl. Pub. No. 2006-0115881-A1 and U.S. Pat. Appl. Pub. No. 2009-0093543-A1. These references also describe details concerning additional modifications that may be required to enable high level production of a particular PUFA, including: 1) manipulation of the activity of acyltransferases that allow for the transfer of omega fatty acids into storage lipid pools (i.e., the TAG fraction); 2) over-expression of desaturases, elongases and diacylglycerol cholinephosphotransferases by use of strong promoters, expression in multicopy, and/or codon-optimization; 3) down-regulation of the expression of specific genes that diminish overall accumulation of the desired PUFA; 4) manipulation of pathways and global regulators that affect production of the desired PUFA; and, 5) "pushing/pulling" within the PUFA biosynthetic pathway. In addition, U.S. Pat. Appl. Pub. No. 2008-0254191-A1, and especially Examples 55 and 56 which are hereby incorporated herein by reference, describes DGLA synthases that possess improved enzymatic activity with respect to their individual Δ9 elongase and/or Δ8 desaturase counterparts, when heterologously expressed in *Yarrowia lipolytica*. Surprisingly, fusing the two independent enzymes together as one fusion protein separated by a linker region increased flux from LA to DGLA, suggesting that the product of Δ9 elongase may be directly channeled as substrate of Δ8 desaturase in the fusion protein.

Although numerous oleaginous yeast could be engineered for production of preferred ω-3/ω-6 PUFAs based on the cited teachings provided above, representative PUFA-producing strains of the oleaginous yeast *Yarrowia lipolytica* are described in Table 2. These strains possess various combinations of the following PUFA biosynthetic pathway genes: delta-4 desaturases, delta-5 desaturases, delta-6 desaturases, delta-12 desaturases, delta-15 desaturases, delta-17 desaturases, delta-9 desaturases, delta-8 desaturases, delta-9 elongases, $C_{14/16}$ elongases, $C_{16/18}$ elongases, $C_{18/20}$ elongases and $C_{20/22}$ elongases, although it is to be recognized that the specific enzymes (and genes encoding those enzymes) introduced and the specific PUFAs produced are by no means limiting to the invention herein. Additionally, the following strains have been deposited with the ATCC: *Y. lipolytica* strain Y2047 (producing ARA; ATCC Accession No. PTA-7186); *Y. lipolytica* strain Y2096 (producing EPA; ATCC Accession No. PTA-7184); *Y. lipolytica* strain Y2201 (producing EPA; ATCC Accession No. PTA-7185); *Y. lipolytica* strain Y3000 (producing DHA ATCC Accession No. PTA-7187); *Y. lipolytica* strain Y4128 (producing EPA; ATCC Accession No. PTA-8614); and *Y. lipolytica* strain Y4127 (producing EPA; ATCC Accession No. PTA-8802). Additionally, *Y. lipolytica* strain Y8406 (producing EPA; ATCC Accession No. PTA-10025), *Y. lipolytica* strain Y8412 (producing EPA; ATCC Accession No. PTA-10026) and *Y. lipolytica* strain Y8259 (producing EPA; ATCC Accession No. PTA-10027) are described in U.S. Provisional Patent Application 61/187,366, filed Jun. 16, 2009 [E.I. duPont de Nemours & Co., Inc., Attorney Docket No. "CL4674", the disclosure of which is hereby incorporated herein by reference.

TABLE 2

Lipid Profile of Representative *Yarrowia lipolytica* Strains Engineered to Produce ω-3/ω-6 PUFAs

| Strain | Reference | ATCC Deposit No. | 16:0 | 16:1 | 18:0 | 18:1 | 18:2 | 18:3 (ALA) | GLA | 20:2 (EDA) | DGLA | ARA | ETA | EPA | DPA | DHA | TFAs % DCW |
|---|---|---|---|---|---|---|---|---|---|---|---|---|---|---|---|---|---|
| Wildtype | U.S. Pat. No. 7,465,564 | #76982 | 14 | 11 | 3.5 | 34.8 | 31 | 0 | 0 | — | — | — | — | — | — | — | — |
| pDMW208 | | — | 11.9 | 8.6 | 1.5 | 24.4 | 17.8 | 0 | 25.9 | — | — | — | — | — | — | — | — |
| pDMW208D62 | | — | 16.2 | 1.5 | 0.1 | 17.8 | 22.2 | 0 | 34 | — | — | — | — | — | — | — | — |
| M4 | U.S. Pat. Appl. Pub. No. 2006-0115881-A1 | — | 15 | 4 | 2 | 5 | 27 | 0 | 35 | — | 8 | 0 | 0 | 0 | — | — | — |
| Y2034 | U.S. Pat. No. 7,588,931 | — | 13.1 | 8.1 | 1.7 | 7.4 | 14.8 | 0 | 25.2 | — | 8.3 | 11.2 | — | — | — | — | — |
| Y2047 | | PTA-7186 | 15.9 | 6.6 | 0.7 | 8.9 | 16.6 | 0 | 29.7 | — | 0 | 10.9 | — | — | — | — | — |
| Y2214 | | — | 7.9 | 15.3 | 0 | 13.7 | 37.5 | 0 | 0 | — | 7.9 | 14 | — | — | — | — | — |
| EU | U.S. Pat. Appl. Pub. No. 2006-0115881-A1 | — | 19 | 10.3 | 2.3 | 15.8 | 12 | 0 | 18.7 | — | 5.7 | 0.2 | 3 | 10.3 | — | — | 36 |
| Y2072 | | — | 7.6 | 4.1 | 2.2 | 16.8 | 13.9 | 0 | 27.8 | — | 3.7 | 1.7 | 2.2 | 15 | — | — | — |
| Y2102 | | — | 9 | 3 | 3.5 | 5.6 | 18.6 | 0 | 29.6 | — | 3.8 | 2.8 | 2.3 | 18.4 | — | — | — |
| Y2088 | | — | 17 | 4.5 | 3 | 2.5 | 10 | 0 | 20 | — | 3 | 2.8 | 1.7 | 20 | — | — | — |
| Y2089 | | — | 7.9 | 3.4 | 2.5 | 9.9 | 14.3 | 0 | 37.5 | — | 2.5 | 1.8 | 1.6 | 17.6 | — | — | — |
| Y2095 | | — | 13 | 0 | 2.6 | 5.1 | 16 | 0 | 29.1 | — | 3.1 | 1.9 | 2.7 | 19.3 | — | — | — |
| Y2090 | | — | 6 | 1 | 6.1 | 7.7 | 12.6 | 0 | 26.4 | — | 6.7 | 2.4 | 3.6 | 26.6 | — | — | 22.9 |
| Y2096 | | PTA-7184 | 8.1 | 1 | 6.3 | 8.5 | 11.5 | 0 | 25 | — | 5.8 | 2.1 | 2.5 | 28.1 | — | — | 20.8 |
| Y2201 | | PTA-7185 | 11 | 16.1 | 0.7 | 18.4 | 27 | 0 | — | 3.3 | 3.3 | 1 | 3.8 | 9 | — | — | — |
| Y3000 | U.S. Pat. No. 7,550,286 | PTA-7187 | 5.9 | 1.2 | 5.5 | 7.7 | 11.7 | 0 | 30.1 | — | 2.6 | 1.2 | 1.2 | 4.7 | 18.3 | 5.6 | — |
| Y4001 | U.S. Pat. Appl. Pub. No. 2009-0093543-A1 | — | 4.3 | 4.4 | 3.9 | 35.9 | 23 | 0 | — | 23.8 | 0 | 0 | 0 | — | — | — | — |
| Y4036 | | — | 7.7 | 3.6 | 1.1 | 14.2 | 32.6 | 0 | — | 15.6 | 18.2 | 0 | 0 | — | — | — | — |
| Y4070 | | — | 8 | 5.3 | 3.5 | 14.6 | 42.1 | 0 | — | 6.7 | 2.4 | 11.9 | — | — | — | — | — |
| Y4086 | | — | 3.3 | 2.2 | 4.6 | 26.3 | 27.9 | 6.9 | — | 7.6 | 1 | 0 | 2 | 9.8 | — | — | 28.6 |
| Y4128 | | PTA-8614 | 6.6 | 4 | 2 | 8.8 | 19 | 2.1 | — | 4.1 | 3.2 | 0 | 5.7 | 42.1 | — | — | 18.3 |
| Y4158 | | — | 3.2 | 1.2 | 2.7 | 14.5 | 30.4 | 5.3 | — | 6.2 | 3.1 | 0.3 | 3.4 | 20.5 | — | — | 27.3 |
| Y4184 | | — | 3.1 | 1.5 | 1.8 | 8.7 | 31.5 | 4.9 | — | 5.6 | 2.9 | 0.6 | 2.4 | 28.9 | — | — | 23.9 |
| Y4217 | | — | 3.9 | 3.4 | 1.2 | 6.2 | 19 | 2.7 | — | 2.5 | 1.2 | 0.2 | 2.8 | 48.3 | — | — | 20.6 |
| Y4259 | | — | 4.4 | 1.4 | 1.5 | 3.9 | 19.7 | 2.1 | — | 3.5 | 1.9 | 0.6 | 1.8 | 46.1 | — | — | 23.7 |
| Y4305 | | — | 2.8 | 0.7 | 1.3 | 4.9 | 17.6 | 2.3 | — | 3.4 | 2 | 0.6 | 1.7 | 53.2 | — | — | 27.5 |
| Y4127 | Int'l. App. Pub. No. WO 2008/073367 | PTA-8802 | 4.1 | 2.3 | 2.9 | 15.4 | 30.7 | 8.8 | — | | | | | | | | |
| Y4184 | | — | 2.2 | 1.1 | 2.6 | 11.6 | 29.8 | 6.6 | — | | | | | | | | |

TABLE 2-continued

Lipid Profile of Representative *Yarrowia lipolytica* Strains Engineered to Produce ω-3/ω-6 PUFAs

| | | | | | | | | |
|---|---|---|---|---|---|---|---|---|
| Y4127 | 4.5 | 3.0 | 3.0 | 2.8 | 18.1 | — | — | — |
| Y4184 | 6.4 | 2.0 | 0.4 | 1.9 | 28.5 | — | — | 24.8 |

Notes:
The term "total fatty acids" ["TFAs"] refer to the sum of all cellular fatty acids that can be derivitized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and triacylglycerols) and from polar lipid fractions but not free fatty acids. The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).
The term "total lipid content" of cells is a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

One of skill in the art will appreciate that the methodology of the present invention is not limited to the *Yarrowia lipolytica* strains described above, nor to the species (i.e., *Yarrowia lipolytica*) or genus (i.e, *Yarrowia*) in which the invention has been demonstrated, as the means to introduce a PUFA biosynthetic pathway into an oleaginous yeast are well known. Instead, any oleaginous yeast capable of producing PUFAs will be equally suitable for use in the present methodologies.

Oleaginous yeast are naturally capable of or engineered to be capable of oil synthesis and accumulation, wherein the total oil content can comprise greater than about 25% of the cellular dry weight, more preferably greater than about 30% of the cellular dry weight, and most preferably greater than about 40% of the cellular dry weight. In alternate embodiments, a non-oleaginous yeast can be genetically modified to become oleaginous such that it can produce more than 25% oil of the cellular dry weight, e.g., yeast such as *Saccharomyces cerevisiae*.

Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

In some embodiments, it may be desirable for the oleaginous yeast to be capable of "high-level production", wherein the organism can produce at least about 5-10% of the desired PUFA (i.e., LA, ALA, EDA, GLA, STA, ETrA, DGLA, ETA, ARA, DPA n-6, EPA, DPA n-3 and/or DHA) in the total lipids. More preferably, the oleaginous yeast will produce at least about 10-25% of the desired PUFA in the total lipids, more preferably at least about 25-35% of the desired PUFA in the total lipids, more preferably at least about 35-45% of the desired PUFA in the total lipids, and most preferably at least about 45-55% of the desired PUFA in the total lipids. The structural form of the PUFA is not limiting; thus, for example, EPA may exist in the total lipids as free fatty acids or in esterified forms such as acylglycerols, phospholipids, sulfolipids or glycolipids.

The PUFA biosynthetic pathway genes and gene products described herein may be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the preferred desaturase and/or elongase sequences. These chimeric genes could then be introduced into appropriate microorganisms via transformation to provide high-level expression of the encoded enzymes.

Accordingly, it is expected that introduction of chimeric genes encoding a PUFA biosynthetic pathway, i.e., the Δ9 elongase/Δ8 desaturase pathway or the delta-6 desaturase/delta-6 elongase pathway described herein, or a portion thereof, under the control of the appropriate promoters will result in increased production of omega-3 and/or omega-6 fatty acids. It is contemplated that it will be useful to express various combinations of the PUFA desaturase and elongase genes together in a host microorganism. It will be obvious to one skilled in the art that the particular gene(s) included within a particular expression cassette(s) will depend on the host cell, its ability to synthesize PUFAs using native desaturases and elongases, the availability of substrate and the desired end product(s). For example, it may be desirable for an expression cassette to be constructed comprising genes encoding one or more of the following enzymatic activities: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and $C_{20/22}$ elongase. As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein (e.g., a wildtype, codon-optimized, synthetic and/or mutant enzyme having appropriate desaturase or elongase activity) can be used directly or indirectly for the production of PUFAs. Direct production of PUFAs occurs wherein the fatty acid substrate is converted directly into the desired fatty acid product without any intermediate steps or pathway intermediates. For example, production of ARA would occur in a host cell which produces or which is provided DLGA, by adding or introducing into said cell an expression cassette that provides Δ5 desaturase activity.

In contrast, multiple genes encoding a PUFA biosynthetic pathway may be used in combination, such that a series of reactions occur to produce a desired PUFA. For example, expression cassette(s) encoding $C_{18/20}$ elongase, Δ5 desaturase, Δ17 desaturase, $C_{20/22}$ elongase and Δ4 desaturase activity would enable a host cell that naturally produces GLA, to instead produce DHA (such that GLA is converted to DGLA by a $C_{18/20}$ elongase; DGLA may then be converted to ARA by a Δ5 desaturase; ARA is then converted to EPA by a Δ17 desaturase, which may in turn be converted to DPA by a $C_{20/22}$ elongase; and DPA would be converted to DHA by a Δ4 desaturase).

It is necessary to create and introduce a recombinant construct comprising an ORF encoding a PUFA biosynthetic pathway gene into a suitable host cell. One of skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from the genes native to the production host.

Transcriptional initiation control regions (also initiation control regions or promoters) useful to drive expression of desaturase and/or elongase ORFs in the desired microbial host cell are well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these genes in the selected host cell is suitable, although transcriptional and translational regions from the host species are particularly useful. Expression in a host cell can be accomplished in an induced or constitutive fashion. Induced expression occurs by inducing the activity of a regulatable promoter operably linked to the gene of interest, while constitutive expression occurs by the use of a constitutive promoter.

When the host cell is yeast, transcriptional and translational regions functional in yeast cells are provided, particularly from the host species. See for example U.S. Pat. Appl. Pub. No. 2006-0115881-A1, corresponding to Intl. App. Pub. No. WO 2006/052870, for preferred transcriptional initiation regulatory regions for use in *Yarrowia lipolytica*. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The 3' non-coding sequences encoding transcription termination regions may be provided in a recombinant construct and may be from the 3' region of the gene from which the initiation region was obtained or from a different gene. A large number of termination regions are known and function satisfactorily in a variety of hosts (when utilized both in the same and different genera and species from which they were derived). Termination regions may also be derived from various genes native to the preferred hosts. The termination region usually is selected more as a matter of convenience rather than because of any particular property. The 3'-region can also be synthetic, as one of skill in the art can utilize available information to design and synthesize a 3'-region sequence that functions as a transcription terminator. A termination site may be unnecessary, but is highly preferred.

Merely inserting a gene into a cloning vector does not ensure its expression at the desired rate, concentration, amount, etc. In response to the need for a high expression rate, many specialized expression vectors have been created by adjusting certain properties that govern transcription, RNA stability, translation, protein stability and location, oxygen limitation, and secretion from the host cell. These properties include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the host cell genome; the final cellular location of the synthesized foreign protein; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell. Each of these types of modifications are encompassed in the present invention, as means to further optimize expression of the PUFA biosynthetic pathway enzymes.

After a recombinant construct is created comprising at least one chimeric gene comprising a promoter, a PUFA biosynthetic pathway gene ORF and a terminator, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a host cell by any standard technique. These techniques include transformation (e.g., lithium acetate transformation [*Methods in Enzymology*, 194:186-187 (1991)]), bolistic impact, electroporation, microinjection, or any other method that introduces the gene(s) of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl Microbiol Biotechnol.* 48(2):232-235 (1997)).

For convenience, a host cell that has been manipulated by any method to take up a DNA sequence, for example, in an expression cassette, will be referred to as "transformed", "transformant" or "recombinant" herein. The transformed host will have at least one copy of the expression construct and may have two or more, depending upon whether the expression cassette is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. Nos. 7,238,482, 7,259,255 and Intl. App. Pub. No. WO 2006/052870.

Following transformation, substrates suitable for the recombinantly expressed desaturases and/or elongases (and optionally other PUFA enzymes that are expressed within the host cell) may be produced by the host either naturally or transgenically, or they may be provided exogenously.

The transformed microbial host cell is grown under conditions that optimize expression of chimeric genes (e.g., encoding desaturases, elongases, etc.) and produce the greatest and the most economical yield of the preferred PUFAs. In general, media conditions that may be optimized include: the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast, are grown in a complex medium (e.g., yeast extract-peptone-dextrose broth (YPD)) or a defined minimal medium that lacks a component necessary for growth and thereby forces selection of the desired expression cassettes (e.g., Yeast Nitrogen Base (DIFCO Laboratories, Detroit, Mich.)).

Fermentation media in the present invention comprise a fermentable carbon source. For use in the method of the invention, the fermentable carbon source is selected from the group consisting of invert sucrose, glucose, fructose and combinations of these, provided that glucose is used in combination with invert sucrose and/or fructose. Invert sucrose may be obtained by hydrolysis of sucrose, which can be obtained from various sources such as sugar cane or sugar beets. The hydrolysis of sucrose to glucose and fructose can be catalyzed by acid (e.g., addition of citric or ascorbic acid) or by enzymes (e.g., invertases or β-fructofuranosidases), as is known in the art.

Fermentation media in the present invention also comprise a suitable nitrogen source. Nitrogen may be supplied from an inorganic (e.g., $(NH_4)_2SO_4$) or organic (e.g., urea or glutamate) source. In addition to appropriate carbon and nitrogen sources, the fermentation medium also contains suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions.

Typically, accumulation of high levels of PUFAs in oleaginous yeast cells requires a two-stage fermentation process, since the metabolic state must be "balanced" between growth and synthesis/storage of fats. Thus, most preferably, a two-stage fermentation process is employed for the production of PUFAs in oleaginous yeast. This process is described in U.S. Pat. No. 7,238,482, as are various suitable fermentation process designs (i.e., batch, fed-batch and continuous) and considerations during growth).

In some aspects herein, the primary product is oleaginous yeast biomass. As such, isolation and purification of the PUFA-containing oils from the biomass may not be necessary (i.e., wherein the whole cell biomass is the product).

However, certain end uses and/or product forms may require partial and/or complete isolation/purification of the PUFA-containing oil from the biomass, to result in partially purified biomass, purified oil, and/or purified PUFA(s). The PUFAs may be found in the host microorganism (e.g., *Yarrowia*) as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6): 463-491 (1992)). A brief review of downstream processing is also provided by A. Singh and O. Ward (*Adv. Appl. Microbiol.*, 45:271-312 (1997)).

In general, methods for the recovery and purification of PUFAs from microbial biomass may include extraction (e.g., U.S. Pat. Nos. 6,797,303 and 5,648,564) with organic solvents, sonication, supercritical fluid extraction (e.g., using carbon dioxide), saponification and physical means such as presses, bead beaters, or combinations thereof. One is referred to the teachings of U.S. Pat. No. 7,238,482 for additional details.

There are a plethora of food and feed products incorporating ω-3 and/or ω-6 fatty acids, particularly e.g., ALA, GLA, ARA, EPA, DPA and DHA. It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils containing ω-3 and/or ω-6 fatty acids will be suitable for use in a variety of food and feed products including, but not limited to: food analogs, meat products, cereal products, baked foods, snack foods and dairy products (see U.S. Pat. Appl. Pub. No. 2006-0094092 for details).

The present compositions may be used in formulations to impart health benefit in medical foods including medical nutritionals, dietary supplements, infant formula and pharmaceuticals. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, *Experiments with Gene Fusions*; Cold Spring Harbor Laboratory: Cold Spring Harbor, N.Y. (1984); and 3.) Ausubel, F. M. et al., *Current Protocols in Molecular Biology*, published by Greene Publishing Assoc. and Wiley-Interscience (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmol" mean micromole(s), "g" means gram(s), "μg" means microgram(s), "ng" means nanogram(s), "nm" means nanometer(s), "rpm" means revolutions per minute.

Figure 2:
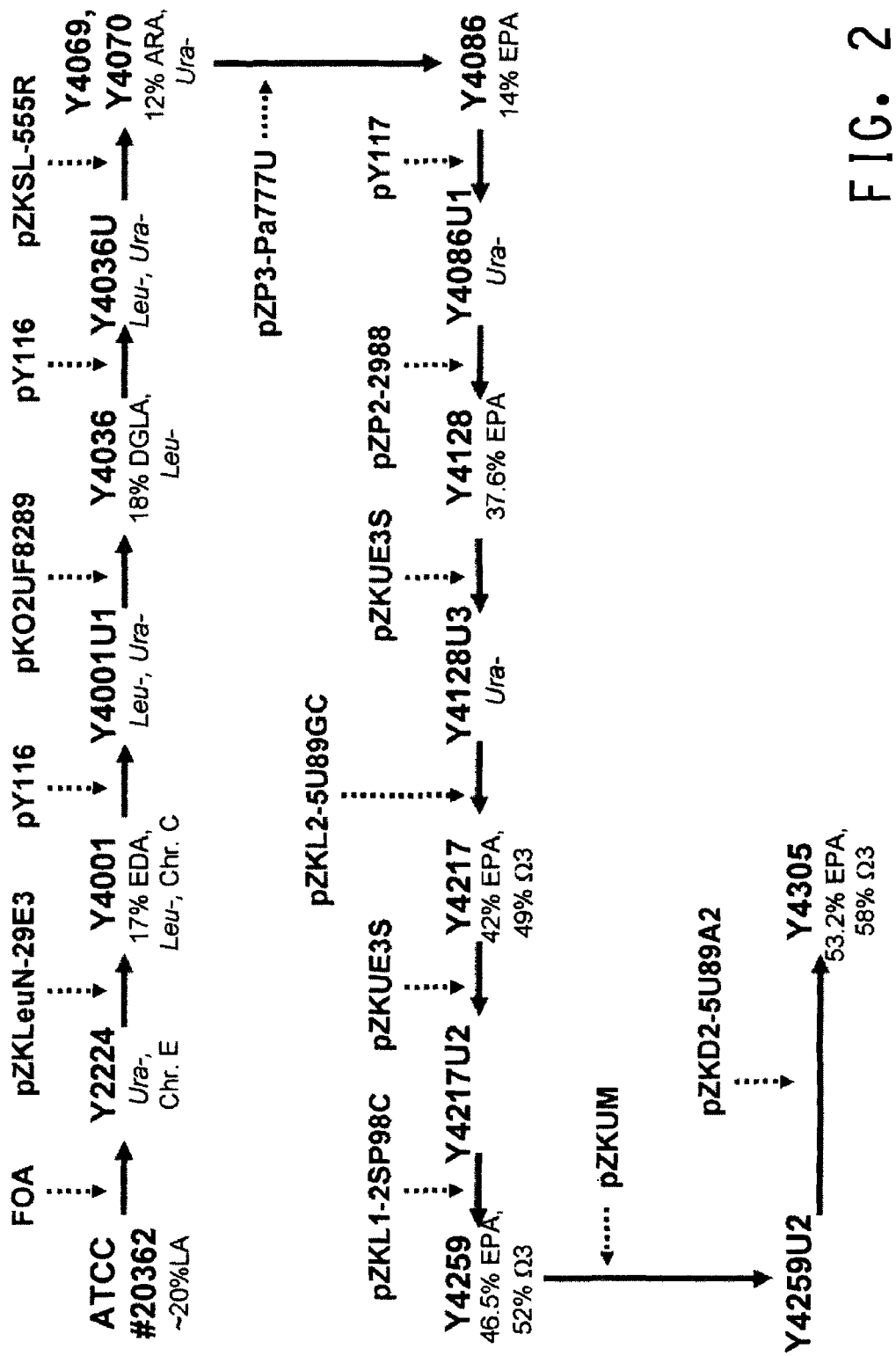
FIG. 2 diagrams the development of *Yarrowia lipolytica* strain Y4305, producing greater than 53% EPA in the total lipid fraction.

The construction of strain Y4305, derived from *Yarrowia lipolytica* ATCC #20362, capable of producing greater than 53% EPA relative to the total lipids via expression of a delta-9 elongase/delta-8 desaturase pathway, is set forth in U.S. Patent Publication No. 2009-009354, published on Apr. 9, 2009, the disclosure of which is hereby incorporated in its entirety. Briefly, as shown in FIG. 2, strain Y4305 was derived from *Yarrowia lipolytica* ATCC #20362 via construction of strain Y2224 (a FOA resistant mutant from an autonomous mutation of the Ura3 gene of wildtype *Yarrowia* strain ATCC #20362), strain Y4001 (producing 17% EDA with a Leu-phenotype), strain Y4001U1 (Leu- and Ura-), strain Y4036 (producing 18% DGLA with a Leu-phenotype), strain Y4036U (Leu- and Ura-), strain Y4070 (producing 12% ARA with a Ura-phenotype), strain Y4086 (producing 14% EPA), strain Y4086U1 (Ura3-), strain Y4128 (producing 37% EPA; deposited with the American Type Culture Collection on Aug. 23, 2007, bearing the designation ATCC PTA-8614), strain Y4128U3 (Ura-), strain Y4217 (producing 42% EPA), strain Y4217U2 (Ura-), strain Y4259 (producing 46.5% EPA), and strain Y4259U2 (Ura-).

The complete lipid profile of strain Y4305 was as follows, wherein the concentration of each fatty acid in the total lipid is expressed as a weight percent of TFAs: 16:0 (2.8%), 16:1 (0.7%), 18:0 (1.3%), 18:1 (4.9%), 18:2 (17.6%), ALA (2.3%), EDA (3.4%), DGLA (2.0%), ARA (0.6%), ETA (1.7%), and EPA (53.2%). The total lipid % dry cell weight ["DCW"] was 27.5.

The final genotype of strain Y4305 with respect to wild type *Yarrowia lipolytica* ATCC #20362 was SCP2-(YALI0E01298g), YALI0C18711g-, Pex10-, YALI0F24167g-, unknown 1-, unknown 3-, unknown 8-, GPD::FmD12::Pex20, YAT1::FmD12::OCT, GPM/FBAIN::FmD12S::OCT, EXP1::FmD12S::Aco, YAT1::FmD12S::Lip2, YAT1::ME3S::Pex16, EXP1::ME3S::Pex20 (3 copies), GPAT::EgD9e::Lip2, EXP1::EgD9eS::Lip1, FBAIN::EgD9eS::Lip2, FBA::EgD9eS::Pex20, GPD::EgD9eS::Lip2, YAT1::EgD9eS::Lip2, YAT1::E389D9eS::OCT, FBAINm::EgD8M::Pex20, FBAIN::EgD8M::Lip1 (2 copies), EXP1::EgD8M::Pex16, GPDIN::EgD8M::Lip1, YAT1::EgD8M::Aco, FBAIN::EgD5::Aco, EXP1::EgD5S::Pex20, YAT1::EgD5S::Aco, EXP1::EgD5S::ACO, YAT1::RD5S::OCT, YAT1::PaD17S::Lip1, EXP1::PaD17::Pex16, FBAINm::PaD17::Aco, YAT1::YICPT1::ACO, GPD::YICPT1::ACO. The structure of the above expression cassettes are represented by a simple notation system of "X::Y::Z", wherein X describes the promoter fragment, Y describes the gene fragment, and Z describes the terminator fragment, which are all operably linked to one another. Abbreviations are as follows: FmD12 is a *Fusarium moniliforme* delta-12 desaturase gene [U.S. Pat. No. 7,504,259]; FmD12S is a codon-optimized delta-12 desaturase gene, derived from *Fusarium moniliforme* [U.S. Pat. No. 7,504,259]; ME3S is a codon-optimized $C_{16/18}$ elongase gene, derived from *Mortierella alpina* [U.S. Pat. No. 7,470,532]; EgD9e is a *Euglena gracilis* delta-9 elongase gene [Intl App. Pub. No. WO 2007/061742]; EgD9eS is a codon-optimized delta-9 elongase gene, derived from *Euglena gracilis* [Intl App. Pub. No. WO 2007/061742]; E389D9eS is a codon-optimized delta-9 elongase gene, derived from *Eutreptiella* sp. CCMP389 [Inn App. Pub. No. WO 2007/061742]; EgD8M is a synthetic mutant delta-8 desaturase [Inn App. Pub. No. WO 2008/073271], derived from *Euglena gracilis* [U.S. Pat. No. 7,256,033]; EgD5 is a *Euglena gracilis* delta-5 desaturase [U.S. Pat. App. Pub. US 2007-0292924-A1]; EgD5S is a codon-optimized delta-5 desaturase gene, derived from *Euglena gracilis* [U.S. Pat. App. Pub. No. 2007-0292924]; RD5S is a codon-optimized delta-5 desaturase, derived from *Peridinium* sp. CCMP626 [U.S. Pat. App. Pub. No. 2007-0271632]; PaD17 is a *Pythium aphanidermatum* delta-17 desaturase [U.S. Pat. No. 7,556, 949]; PaD17S is a codon-optimized delta-17 desaturase, derived from *Pythium aphanidermatum* [U.S. Pat. No. 7,556, 949]; and, YICPT1 is a *Yarrowia lipolytica* diacylglycerol cholinephosphotransferase gene [Int'l App. Pub. No. WO 2006/052870].

Strain Y4305-F1B1 was derived from strain Y4305 as follows. Strain Y4305 was subjected to transformation with a dominant, non-antibiotic marker for *Yarrowia lipolytica* based on sulfonylurea ["$SU^R$"] resistance. More specifically, the marker gene is a native acetohydroxyacid synthase ("AHAS" or acetolactate synthase; E.C. 4.1.3.18) that has a single amino acid change, i.e., W497L, that confers sulfonyl urea herbicide resistance (SEQ ID NO:292 of Intl. App. Pub. No. WO 2006/052870). AHAS is the first common enzyme in the pathway for the biosynthesis of branched-chain amino acids and it is the target of the sulfonylurea and imidazolinone herbicides.

The random integration of the $SU^R$ genetic marker into *Yarrowia* strain Y4305 was used to identify those cells having increased lipid content when grown under oleaginous conditions relative to the parent Y4305 strain.

Specifically, a mutated AHAS gene, described above, was introduced into *Yarrowia* cells as a linear DNA fragment. The AHAS gene integrates randomly throughout the chromosome at any location that contains a double stranded-break that is also bound by the Ku enzymes. Non-functional genes or knockout mutations were generated when the $SU^R$ fragment integrated within the coding region of a gene. Every gene is a potential target for down-regulation. Thus, a random integration library in *Yarrowia* cells was made and $SU^R$ mutant cells that were identified. Candidates were evaluated based on DCW (g/L), FAMEs % DCW, EPA % TFAs and EPA % DCW.

Out of the 48 mutant cultures evaluated, only three of the cultures (i.e., F1B1 [15.1 EPA % DCW], F1B5 [15.6 EPA % DCW], and F1 G6 [16.1 EPA % DCW] were selected for further evaluation in triple flask analysis. The results of the triple flask analysis are summarized in Table 3.

TABLE 3

Shake Flask Evaluation Of Individual Y4305 $SU^R$ Mutants

| Strain | DCW (g/L) | TFAs % DCW | EPA % TFAs | EPA % DCW |
|---|---|---|---|---|
| Y4305 | 6.8 | 25.1 | 50.3 | 12.7 |
| Y4305 F1B1 | 6.9 | 27.9 | 53.1 | 14.8 |
| Y4305 F1B5 | 6.9 | 27.7 | 53.0 | 14.7 |
| Y4305 F1G6 | 7.2 | 27.8 | 52.4 | 14.6 |

Since strain Y4305-F1B1 possessed the highest EPA productivity ["EPA % DCW"] and lipid content ["TFAs % DCW"] of those evaluated, this mutant was selected for further evaluation under two liter fermentation conditions (parameters similar to those of U.S. Pat. Appl. Pub. No. 2009-009354-A1, Example 10).

Average EPA productivity ["EPA % DCW"] for strain Y4305 was 50-56, as compared to 50-52 for strain Y4305-F1B1. Average lipid content ["TFAs % DCW"] for strain Y4305 was 20-25, as compared to 28-32 for strain Y4305-F1B1. Thus, lipid content was increased 29-38% in strain Y4503-F1B1, with minimal impact upon EPA productivity.

Example 1

Production of Omega-3/Omega-6 Fatty Acids with Fructose as Carbon Source

This Example illustrates the production of omega-3/omega-6 Fatty acids by *Yarrowia lipolytica* strain Y4305 using fructose as a carbon source.

*Yarrowia lipolytica* strain Y4305, described above, was cultured in a medium containing: 6.7 g/L yeast nitrogen base without amino acids but with ammonium sulfate, 5 g/L yeast extract, 6 g/L $KH_2PO_4$, 2 g/L $K_2HPO_4$, 1.5 g/L $MgSO_4.7H_2O$, 1.5 mg/L thiamine-HCl, and 20 g/L fructose. The Y4305 cells were cultured in 25 mL of this medium in a 125-mL flask in a shaker incubator for 48 h at 30° C. and 250 rpm. Then, 6 mL of the resulting culture was centrifuged to collect cell samples. The collected cell samples were resuspended in 25 mL of a high fructose medium containing: 80 g/L fructose, 27 g/L $K_2HPO_4$, and 6.3 g/L $KH_2PO_4$. The high fructose medium culture was incubated for 5 days at 30° C. and 250 rpm.

For fatty acid ["FA"] analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I. *Arch Biochem Biophys.*, 276(1):38-46 (1990)) and subsequently analyzed with a Hewlett-Packard 6890 gas chromatograph (GC) (Agilent Technologies Inc., Wilmington, Del.) fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 µL of a 1% solution) and a known amount of C15:0 triacylglycerol (C15:0 TAG; Cat. No. T-145, Nu-Check Prep, Elysian, Minn.) were added to the sample, and the sample was vortexed and rocked for 30 min at 50° C. After adding 3 drops of 1.0 M NaCl and 400 µL of hexane, the sample was vortexed and spun. The upper layer was removed and analyzed by GC.

FAME peaks recorded via GC analysis were identified by their retention times, when compared to that of known fatty acids, and quantified by comparing the FAME peak areas with that of the internal standard (C15:0 TAG) of known amount. Thus, the approximate amount (µg) of any fatty acid FAME ["µg FAME"] was calculated according to the formula: (area of the FAME peak for the specified fatty acid/area of the standard FAME peak)*(µg of the standard C15:0 TAG), while the amount (µg) of any fatty acid ["µg FA"] was calculated according to the formula: (area of the FAME peak for the specified fatty acid/area of the standard FAME peak)*(µg of the standard C15:0 TAG)*0.9503, since 1 µg of C15:0 TAG was equal to 0.9503 µg fatty acids. Note that the 0.9503 conversion factor was an approximation of the value determined for most fatty acids, which range between 0.95 and 0.96.

The lipid profile, summarizing the amount of each individual fatty acid as a weight percent of TFAs, was determined by dividing the individual FAME peak area by the sum of all FAME peak areas and multiplying by 100.

For dry cell weight (DCW) determination, 10 mL of culture was harvested by centrifugation for 5 min at 4000 rpm in a Beckman GH-3.8 rotor in a Beckman GS-6R centrifuge (Beckman Coulter Inc., Fullerton, Calif.). The pellet was resuspended in 25 mL of water and re-harvested as described above. The washed pellet was re-suspended in 20 mL of water and transferred to a pre-weighed aluminum pan. The cell suspension was dried overnight in a vacuum oven at 80° C., after which the weight of the cells was determined.

Total lipid content of cells, based on the fatty acid methyl esters ["FAME % DCW"], was calculated and considered in conjunction with data tabulating the concentration of each fatty acid methyl ester as a weight percent of FAMEs ["% FAMEs"] and the EPA content, expressed in the form of the EPA methyl ester, as a percent of the dry cell weight ["EPA % DCW"]. The resulting data is presented in Table 4, which summarizes the total dry cell weight of the cells ["DCW'], the concentration of each fatty acid methyl ester as a weight percent of FAMEs ["% FAMEs"] and the EPA methyl ester content as a percent of the dry cell weight ["EPA % DCW"]. More specifically, fatty acids are identified as 16:0 (palmitate), 16:1 (palmitoleic acid), 18:0 (stearic acid), 18:1 (oleic acid), 18:2 (linoleic acid), 18:3 (ALA), 20:2 (EDA), 20:3 (DGLA), 20:4 (ARA), ETrA, 20:4, 20:4 (n-1) (ETA), and 20:5 (EPA).

Example 2

Production of Omega-3/Omega-6 Fatty Acids with Invert Sugar as Carbon Source This Example illustrates the production of omega-3/omega-6 fatty acids by *Yarrowia lipolytica* strain Y4305 using invert sugar as a carbon source.

*Yarrowia lipolytica* strain Y4305, described above, was cultured in a medium containing: 6.7 g/L yeast nitrogen base without amino acids but with ammonium sulfate, 5 g/L yeast extract, 6 g/L $KH_2PO_4$, 2 g/L $K_2HPO_4$, 1.5 g/L $MgSO_4.7H_2O$, 1.5 mg/L thiamine-HCl, and 20 g/L invert sugar (53.51% conversion, containing 46.49% sucrose, 26.75% glucose and 26.75% fructose; obtained from MP Biochemicals, Solon, Ohio). The Y4305 cells were cultured in 25 mL of this medium in a 125-mL flask in a shaker incubator for 48 h at 30° C. and 250 rpm. Then, 6 mL of the resulting culture was centrifuged to collect cell samples. The collected cell samples were resuspended in 25 mL of a high invert sugar medium containing: 80 g/L invert sugar, 27 g/L $K_2HPO_4$, and 6.3 g/L $KH_2PO_4$. The high invert sugar medium culture was incubated for 5 days at 30° C. and 250 rpm. Fatty acid analysis was done as described in Example 1 and the results are summarized in Table 4.

Example 3, Comparative

Production of Omega-3/Omega-6 Fatty Acids with Glucose as Carbon Source

This comparative Example illustrates the production of omega-3/omega-6 Fatty acids by *Yarrowia lipolytica* strain Y4305 using glucose as a carbon source.

*Yarrowia lipolytica* strain Y4305, described above, was cultured in a medium containing: 6.7 g/L yeast nitrogen base without amino acids but with ammonium sulfate, 5 g/L yeast extract, 6 g/L $KH_2PO_4$, 2 g/L $K_2HPO_4$, 1.5 g/L $MgSO_4.7H_2O$, 1.5 mg/L thiamine-HCl, and 20 g/L glucose. The Y4305 cells were cultured in 25 mL of this medium in a 125-mL flask in a shaker incubator for 48 h at 30° C. and 250 rpm. Then, 6 mL of the resulting culture was centrifuged to collect cell samples. The collected cell samples were resuspended in 25 mL of a high glucose medium containing: 80 g/L glucose, 27 g/L $K_2HPO_4$, and 6.3 g/L $KH_2PO_4$. The high glucose medium culture was incubated for 5 days at 30° C. and 250 rpm. Fatty acid analysis was done as described in Example 1 and the results are summarized in Table 4.

The data in Table 4 is the average from two cultures. As can be seen from the data in Table 4, the cultures grown in glucose medium (Example 3, Comparative) and fructose medium (Example 1) produced similar amounts of biomass, based on dry cell weight. These cultures also produced similar fatty acid compositions and total lipid content. The lipid and EPA production were only slightly lower with fructose compared to glucose. The biomass produced by the culture grown in invert sugar medium (Example 2) was significantly lower that that obtained with glucose medium or fructose medium. The lipid content produced by cultures grown in the invert sugar medium was similar to that of cultures grown in glucose medium of fructose medium, but the EPA content produced by the cultures grown in invert sugar was lower. However, the amount of sugar available in the invert sugar culture was significantly lower than in the other cultures because the invert sugar used was only 53.51% converted, and therefore contained 46.49% sucrose, which was not utilized by the cells.

TABLE 4

Results of Fatty Acid Analysis

| Example | DCW (g/L) | FAME % DCW | 16:0[a] palmitic | 16:1[a] | 18:0[a] stearic | 18:1[a] oleic | 18:2[a] linoleic | 18:3[a] (n-3) ALA | 20:2[a] EDA | 20:3[a] (n-6) DGL-A | 20:4[a] ARA | Etr[a] | 20:4[a] | 20:4[a] (n-3) ETA | 20:5[a] EPA | EPA % DCW |
|---|---|---|---|---|---|---|---|---|---|---|---|---|---|---|---|---|
| Example 1 | 6.1 | 26.1 | 2.8 | 0.8 | 1.7 | 6.6 | 19.8 | 3.9 | 3.4 | 1.9 | 0.3 | 0.9 | 1.0 | 1.9 | 50.5 | 13.2 |
| Example 2 | 4.0 | 25.1 | 3.3 | 0.9 | 1.6 | 7.8 | 20.2 | 4.5 | 3.9 | 1.8 | 0.3 | 1.1 | 1.2 | 1.9 | 47.4 | 11.9 |
| Example 3, Comparative | 5.9 | 26.5 | 2.4 | 0.8 | 1.5 | 6.4 | 19.2 | 3.9 | 3.4 | 1.9 | 0.3 | 0.9 | 1.2 | 1.9 | 51.8 | 13.7 |

[a]reported as % FAME

Examples 4-7

Production of Omega-3/Omega-6 Fatty Acids in a Fermentor Using Glucose, Fructose, a Mixture of Glucose and Fructose, and Invert Sucrose as Carbon Sources These Examples demonstrate the production of omega-3 and omega-6 fatty acids by *Yarrowia lipolytica* strain Y4305-F1B1 grown in a 10-L fermentor on various carbon sources.

Seed culture: To prepare the seed culture in a shake flask, thawed frozen glycerol stock of the genetically engineered strain of *Yarrowia lipolytica* Y4305-F1B1 (0.5 mL) was transferred to a 2-L shake flask containing 500 mL complex medium, which contained D-glucose (20 g/L), $KH_2PO_4$ (6.0 g/L), $Na_2HPO_4.12H_2O$ (3.3 g/L), $MgSO_4.7H_2O$ (1.5 g/L) and thiamine.HCl (1.5 mg/L). The flask culture was incubated for 24-36 h at 30° C. and 300 rpm to an optical density at 600 nm ($OD_{600}$) of at least 4.

Fermentation: A 14-liter Biostat® C fermentor (B.Braun Biotech International, Germany) was used for these fermentation experiments. The fermentation is a 2-stage fed-batch process. In the first stage, the yeast were cultured under conditions that promote rapid growth to a high cell density; the culture medium comprised a carbon source, various nitrogen sources, trace metals and vitamins. In the second stage, the yeast were starved for nitrogen and continuously fed the carbon source to promote lipid and PUFA accumulation.

Specifically, the shake-flask seed culture (500 mL, $OD_{600} \geq 4$) from above was transferred to the 14-liter Biostat® B fermentor to initiate the fermentation (t=0 h) containing 5.2-L of fresh fermentation medium. The fresh fermentation medium included yeast extract (5.0 g), $KH_2PO_4$ (6.0 g), $Na_2HPO_4.12H_2O$ (3.3 g), $MgSO_4.7H_2O$ (1.5 g), thiamine. HCl (1.5 mg), a carbon source (initial concentration of approximately 50 g/L), trace metal solution (100×) (24 mL), and antifoam 204 (0.2 mL; Sigma Aldrich, St. Louis, Mo.). The carbon sources used were 50% (w/w) glucose (Comparative Example 4), 50% (w/w) fructose (Example 5), a 25% (w/w) glucose, 25% (w/w) fructose mixture (Example 6), and 50% (w/w) invert sucrose, from Cosan, Brazil; Acucar Ref. Liquid Invertido, Lot # DO8D24A1 BA (Example 7). The trace metal solution (100×) contained citric acid (10 g/L), $CaCl_2.2H_2O$ (1.5 g/L), $FeSO_4.7H_2O$ (10 g/L), $ZnSO_4.7H_2O$ (0.39 g/L), $CuSO_4.5H_2O$ (0.38 g/L), $CoCl_2.6H_2O$ (0.20 g/L), and $MnCl_2.4H_2O$ (0.30 g/L). The dissolved oxygen concentration ($pO_2$) was controlled above zero by cascade-controlling the impeller speed between 80 and 1200 rpm.

Carbon source feeding (i.e., 50% w/w glucose, Comparative Example 4; 50% w/w fructose, Example 5; 25% w/w glucose and 25% w/w fructose, Example 6, and 50% w/w invert sucrose, Example 7), commenced when the concentration in the medium decreased to approximately 20 g/L. The carbon source concentrations were maintained within 15-30 g/L during the entire fermentation process.

The acid for the pH control was $H_3PO_4$ (20% w/v). The base for the pH control was KOH (56% w/v). The temperature was controlled at 30-32° C. and pH value was controlled between 5-7, respectively.

Fermentation samples (~40 mL) were taken every 4-15 hours throughout the fermentation to measure the intracellular lipid concentration, lipid profile, optical density of cells, dry cell weight ["dcw"], concentrations of glucose, major cations, and organic acids. The intracellular lipid of the Yarrowia cells was extracted out with methanol and chloroform and its concentration and profiles were determined by GC, according to the methodology described in Example 1.

Results from these fermentations are provided in Table 5.

TABLE 5

Total Lipid and EPA Produced by Fermentation using Yarrowia lipolytica Strain Y4305-F1B1 Grown on Various Carbon Sources

| Example | Strain | Carbon Source | Total Lipid (% dcw) | EPA (% total lipid) | EPA (% dcw) |
|---|---|---|---|---|---|
| 4 | Y4305-F1B1 | 50% (w/w) Glucose | 27.9 | 46.4 | 12.9 |
| 5 | Y4305-F1B1 | 50% (w/w) Fructose | 24.6 | 48.7 | 12.0 |
| 6 | Y4305-F1B1 | 25% (w/w) Glucose, 25% (w/w) Fructose | 24.5 | 50.8 | 12.4 |
| 7 | Y4305-F1B1 | 50% (w/w) Inverted Sucrose | 17.7 | 57.3 | 10.1 |

All fermentation runs were successful, thereby demonstrating the ability of Yarrowia lipolytica to grow on fructose, fructose plus glucose and invert sucrose. The effect of the alternative carbon feeds on cumulative carbon fed and on the concentration of each of the sugar components was examined. Average glucose concentration was significant only for the fermentation fed 50% (w/w) glucose (Comparative Example 4), since this glucose concentration was controlled at an average of 20 g/L. In all other fermentations, glucose concentration decreased to approximately zero relatively rapidly. For the 25% (w/w) glucose plus 25% (w/w) fructose fermentation (Example 6), the fructose concentration built until the glucose concentration was nearly zero, and it then began to fall to a low but positive value. For the commercial invert sucrose fermentation (Example 7), both glucose and fructose concentrations dropped to nearly zero (although glucose concentration dropped faster than fructose concentrations) and sucrose accumulated throughout the run. The invert sucrose used contained approximately 5% by weight sucrose. As is well known to one of skill in the art, the amount of sucrose present in the invert sucrose will depend on the degree of hydrolysis.

The effect of the alternative carbon sources on total lipid as a percent of dry cell weight, and on EPA as a percent of total lipid (Table 5) was also examined. Based on these results, demonstrating successful accumulation of oil and PUFAs, one of skill in the art will recognize that 50% (w/w) fructose (Example 5), a combination of 25% (w/w) glucose plus 25% (w/w) fructose (Example 6), and commercial invert sucrose (Example 7) are all viable alternative carbon sources that can be utilized for fermentation of Yarrowia lipolytic, in place of glucose to produce omega-3 and omega-6 fatty acids.

Examples 8-10

Production of Omega-3/Omega-6 Fatty Acids in a Fermentor Using Mixtures of Glucose, Fructose, and Sucrose as Carbon Sources These Examples demonstrate the production of omega-3 and omega-6 fatty acids by Yarrowia lipolytica strain Y4305-F1B1 grown in a 10-L fermentor on various mixtures of glucose, fructose, and sucrose as carbon sources. Sucrose was included in the mixtures to simulate invert sucrose, which typically contains some unhydrolyzed sucrose.

A set of 10-L scale fermentation runs were completed utilizing the following alternative carbon sources for growth and production: Example 8, 25% (w/w) glucose plus 25% (w/w) fructose; Example 9, 25% (w/w) glucose plus 25% (w/w) fructose plus (nominally) 1% (w/w) sucrose; and Example 10, 25% (w/w) glucose plus 25% (w/w) fructose plus nominally 5% (w/w) sucrose. More specifically, fermentation runs were conducted as described in Examples 4-7 using the carbon sources listed above. The feed rate for all carbon sources used in Examples 8-10 were comparable, and the feed rate was approximately the same as the feed rate used in Examples 4-7.

The carbon feed compositions were analyzed by HPLC to determine the actual concentrations of the components in the feeds. The feed that was to contain nominally 1% (w/w) sucrose actually contained 2% (w/w) sucrose upon HPLC analysis. All the other carbon feed compositions were as expected within experimental error.

Results from the fermentation runs were analyzed as described in Examples 4-7. With respect to the effect of alternative carbon feeds on cumulative carbon fed and on the concentration of each of the sugar components, all experimental runs were similar. Specifically, glucose concentration decreased rapidly to near zero; fructose concentration built until the glucose concentration was nearly zero and then it began to fall to a low but positive value. Sucrose accumulated throughout the 1% (w/w) sucrose fermentation run (Example 9) and the 5% (w/w) sucrose fermentation run (Example 10) because sucrose is not utilized by the *Yarrowia lipolytica* strain used.

The effect of the alternative carbon sources on total lipid as a percent of dry cell weight and on EPA as a percent of total lipid (Table 6) was examined. Based on these results, demonstrating successful accumulation of oil and PUFAs, one of skill in the art will recognize that 25% (w/w) glucose plus 25% (w/w) fructose (Example 8), 25% (w/w) glucose plus 25% (w/w) fructose plus (nominally) 1% (w/w) sucrose (Example 9), and 25% (w/w) glucose plus 25% (w/w) fructose plus nominally 5% (w/w) sucrose (Example 10) are all viable alternate carbon sources that can be utilized for fermentation of *Yarrowia lipolytica* in place of glucose to produce omega-3 and omega-6 fatty acids.

TABLE 6

Total Lipid and EPA Produced by Fermentation using *Yarrowia lipolytica* Strain Y4305-F1B1 Grown on Various Carbon Sources

| Example | Strain | Carbon Source | Total Lipid (% dcw) | EPA (% total lipid) | EPA (% dcw) |
| --- | --- | --- | --- | --- | --- |
| 8 | Y4305-F1B1 | 25% (w/w) Glucose, 25% (w/w) Fructose | 20.3 | 48.4 | 9.8 |
| 9 | Y4305-F1B1 | 25% (w/w) Glucose, 25% (w/w) Fructose, 1% (w/w) Sucrose | 24.7 | 47.8 | 11.8 |
| 10 | Y4305-F1B1 | 25% (w/w) Glucose, 25% (w/w) Fructose, 5% (w/w) Sucrose | 26.5 | 44.5 | 11.8 |

What is claimed is:

1. A method for producing polyunsaturated fatty acids comprising:
    a) providing a transgenic oleaginous yeast that does not utilize sucrose as a carbon source and which produces at least 25% of its dry cell weight as oil; said yeast comprising genes encoding a functional polyunsaturated fatty acid biosynthetic pathway;
    b) growing the yeast of step (a) in the presence of invert sucrose comprising sucrose, about 25% to 50% by weight (w/w) glucose, and about 25% to 50% (w/w) fructose, whereby polyunsaturated fatty acids are produced; and
    c) optionally, recovering the polyunsaturated fatty acids.

2. The method of claim 1 wherein the polyunsaturated fatty acids are selected from the group consisting of omega-3 fatty acids, omega-6 fatty acids, and combinations thereof.

3. The method of claim 1 wherein the genes encoding a functional polyunsaturated fatty acid biosynthetic pathway are selected from the group consisting of: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and $C_{20/22}$ elongase.

4. The method of claim 1 wherein the oleaginous yeast is selected from the group consisting of *Yarrowia, Candida, Rhodotorula, Rhodosporidium, Cryptococcus, Trichosporon* and *Lipomyces*.

5. The method of claim 4 wherein the oleaginous yeast is *Yarrowia lipolytica*.

6. The method of claim 1 wherein the invert sucrose comprises 25% (w/w) glucose and 25% (w/w) fructose.

7. The method of claim 1 wherein the invert sucrose comprises 1 to 5% (w/w) sucrose.

* * * * *